US007029496B2

(12) United States Patent
Rakos et al.

(10) Patent No.: US 7,029,496 B2
(45) Date of Patent: Apr. 18, 2006

(54) INTERLOCKING ENDOLUMINAL DEVICE

(75) Inventors: Ronald Rakos, Neshanic Station, NJ (US); Krzysztof Sowinski, Wallington, NJ (US)

(73) Assignee: Scimed Life Systems, Inc., Maple Grove, MN (US)

( * ) Notice: Subject to any disclaimer, the term of this patent is extended or adjusted under 35 U.S.C. 154(b) by 427 days.

(21) Appl. No.: 10/010,628

(22) Filed: Nov. 7, 2001

(65) Prior Publication Data

US 2003/0088306 A1    May 8, 2003

(51) Int. Cl.
*A61F 2/06* (2006.01)
(52) U.S. Cl. .................................... 623/1.35
(58) Field of Classification Search .............. 623/1.35, 623/1.15, 1.13
See application file for complete search history.

(56) References Cited

U.S. PATENT DOCUMENTS

| 5,575,818 | A |   | 11/1996 | Pinchuk |   |
|---|---|---|---|---|---|
| 5,683,449 | A |   | 11/1997 | Marcade |   |
| 5,755,773 | A |   | 5/1998 | Evans et al. |   |
| 5,961,548 | A |   | 10/1999 | Shmulewitz |   |
| 6,015,431 | A | * | 1/2000 | Thornton et al. | 623/1.14 |
| 6,017,363 | A | * | 1/2000 | Hojeibane | 623/23.7 |
| 6,019,788 | A | * | 2/2000 | Butters et al. | 623/1.35 |
| 6,143,002 | A |   | 11/2000 | Vietmeier |   |
| 6,165,213 | A |   | 12/2000 | Goicoechea et al. |   |
| 6,193,745 | B1 |   | 2/2001 | Fogarty et al. |   |
| 6,210,429 | B1 |   | 4/2001 | Vardi et al. |   |
| 6,302,908 | B1 |   | 10/2001 | Parodi |   |
| 6,325,826 | B1 |   | 12/2001 | Vardi et al. |   |
| 2001/0037142 | A1 |   | 11/2001 | Stelter et al. |   |

OTHER PUBLICATIONS

U.S. Appl. No. 09/898,936, filed Jul. 3, 2001 entitled Implant Having Improved Fixation to a Body Lumen and Method for Implanting the Same.
International Search Report for corresponding International Application PCT/US02/33879, mail date Oct. 9, 2003.

* cited by examiner

*Primary Examiner*—(Jackie) Tan-Uyen T. Ho
(74) *Attorney, Agent, or Firm*—RatnerPrestia

(57) ABSTRACT

An endoluminal device comprises at least a first member and a second member, which may be modular. The first member comprises a first trunk portion, a first midsection comprising a first opening, and a first leg portion. The second member comprises a second trunk portion, a second midsection comprising a second opening, and a second leg portion. The device has an assembled configuration in which the first member and second member are interlocked with one another with the second trunk portion coaxially contained within the first trunk portion, the second leg portion protruding through the first opening, and the second opening facing the first leg portion. The second midsection may have a leg stump portion that protrudes into the first leg portion of the first member in the assembled configuration. A system and method for deploying the device may use identical catheters for deploying the two members.

36 Claims, 2 Drawing Sheets

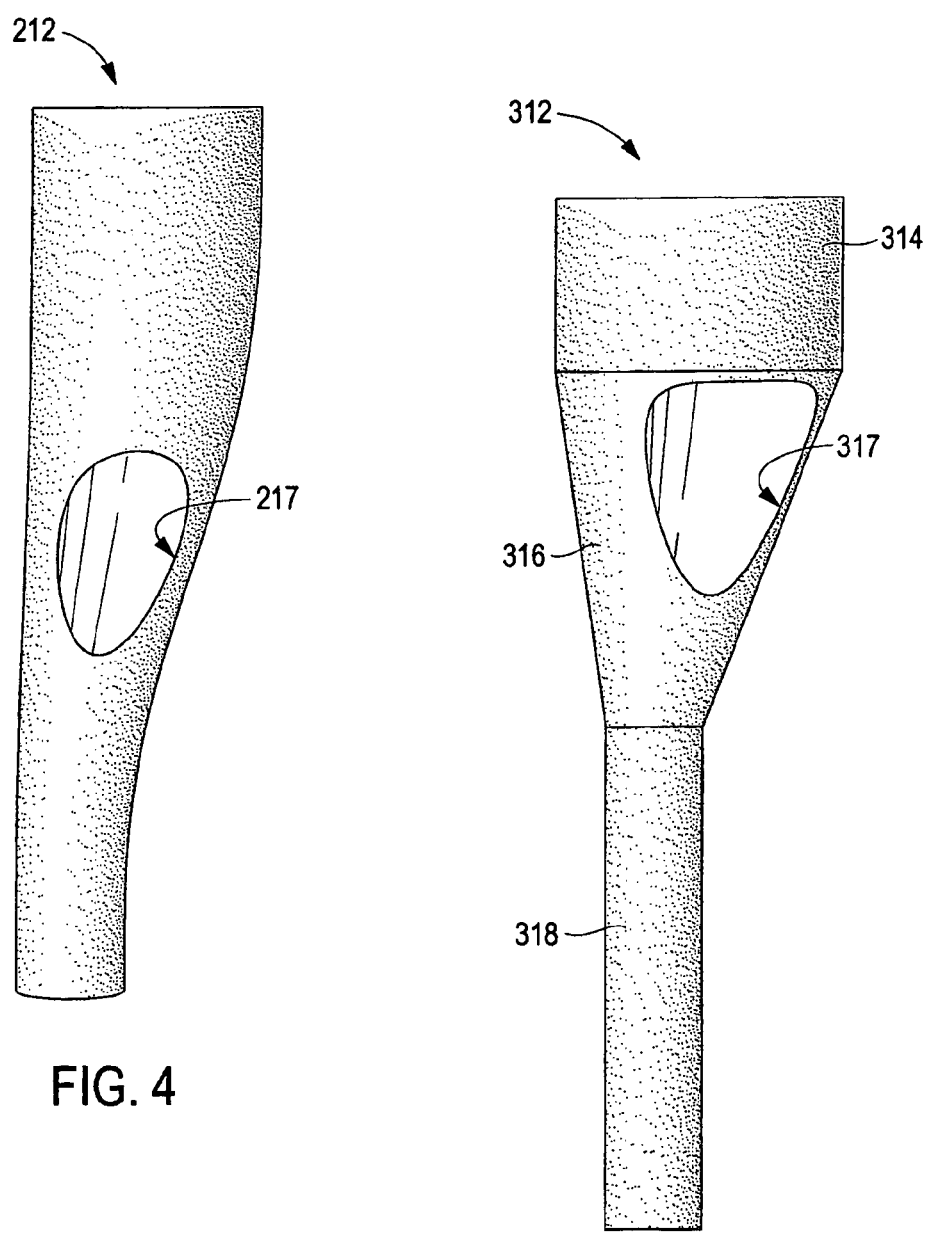

INTERLOCKING ENDOLUMINAL DEVICE

TECHNICAL FIELD

This invention relates generally to endoluminal devices and, more specifically, to endoluminal devices such as stents, grafts, and stent-grafts.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. As used herein, however, the term "stent" is a shorthand reference referring to a covered or uncovered such device.

A covered stent may be used, for example, to treat a vascular aneurysm by removing the pressure on a weakened part of an artery so as to reduce the risk of rupture. Typically, a stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to this access location, whereas the term "distal" is used to refer to portions farther from the access location.

When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Among the many applications for stent-grafts is for deployment in branching lumen, and more specifically for bifurcated lumen, such as for repair of abdominal aortic aneurysms (AAA). Various stent-graft configurations are known in the art for bifurcated applications, including single-piece ("unitary") designs and modular designs. Bifurcated devices, however, may involve special tooling and procedures for their manufacture that result in high cycle time and low yields, may utilize relatively large-profile delivery systems or specialized delivery systems, and in general may be relatively complex in design and implementation. Modular devices typically also have a risk of leaks in the seals between the modular components. Thus, it is desirable to provide a modular endoluminal device, such as a bifurcated stent-graft, that accommodates a branching flow path yet minimizes drawbacks often associated with bifurcated and/or modular devices.

SUMMARY OF THE INVENTION

In accordance with this invention, there is provided an endoluminal device comprising a first member and a second member. The first member comprises a first trunk portion, a first midsection comprising a first opening, and a first leg portion. The second member comprises a second trunk portion, a second midsection comprising a second opening, and a second leg portion. The device has an assembled configuration in which the first member and second member are interlocked with one another with the second trunk portion coaxially contained within the first trunk portion, the second leg portion protruding through the first opening, and the second opening facing the first leg portion. The second midsection may further comprise a leg stump portion that protrudes into the first leg portion of the first member in the assembled configuration.

The first member and the second member each may further comprise a stent having a covering inside, outside, or inside and outside of the stent. The covering may comprise a textile, a plastic, or a combination thereof. The first member may comprise an uncovered portion of the stent, such as an uncovered portion adapted to be located at an intersection of a renal lumen with the aorta. The first member may comprise a partial inside covering and the second member may comprise an outside covering, where the first member has no inside covering in an interlocking portion adapted to contact the outside covering of the second member.

The invention also comprises a modular endoluminal device for deployment in a body lumen comprising a main lumen, a first branch lumen, a second branch lumen, and an internal fluid flowing in a first direction from the main lumen into the first and second branch lumens. The device comprises a first member for directing the fluid from the main lumen into the first branch lumen and a second member for directing the fluid from the main lumen into the second branch lumen. The device, therefore, accommodates a branching fluid flow. The first member and the second member are adapted to interlock together such that the fluid flow forces the second member against the first member in a sealing relationship. The second member may comprise at least one impingement area on which the fluid flow impinges to force the second member against the first member.

A system for deployment of an endoluminal device of this invention may comprise a first introducer for deploying the first member into a body lumen and having a first profile; and a second introducer, having a second profile essentially identical to the first profile, for deploying the second member into the body lumen.

The invention also comprises a method of deploying an endoluminal device of the present invention in a deployment location in a branched lumen comprising a main lumen, a first branch lumen, and a second branch lumen. The method comprises the steps of inserting a first introducer containing the first member into the branched lumen from a first proximal location, and deploying the first member with the first trunk portion in the main lumen and the first leg portion in the first branch lumen. A second introducer containing the second member is then inserted into the branched lumen from a second proximal location and the second member is deployed such that the second member is interlocked with the first member in the assembled configuration with the second trunk portion coaxially contained within the first trunk portion, the second leg portion protruding through the first opening into the second branch lumen, and the second opening facing the first leg portion.

It is to be understood that both the foregoing general description and the following detailed description are exemplary, but not restrictive, of the invention.

BRIEF DESCRIPTION OF THE DRAWINGS

The invention is best understood from the following detailed description when read in connection with the accompanying drawing, in which:

FIG. 3 is a cross-sectional illustration of a portion of an exemplary wall taken across line 3—3 in FIG. 1;

FIG. 4 is a plan view illustration of an exemplary tapered member of the present invention; and FIG. 5 is a plan view illustration of an exemplary member of the present invention having a straight leg design.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1:
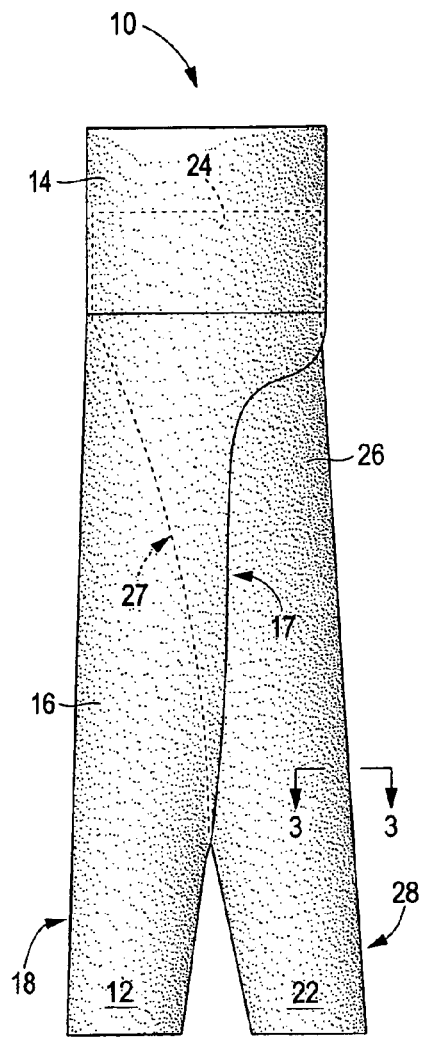
FIG. 1 is a plan view illustration showing an exemplary embodiment of a device of the present invention.

Referring now to FIG. 1, there is shown an exemplary endoluminal device 10 of this invention. Device 10 may be said to be "modular" in that it is constructed of more than one standardized, although not necessarily identical, units. In particular, device 10 comprises two members 12 and 22. First member 12 comprises a first trunk portion 14, a first midsection 16 comprising a first opening 17, and a first leg portion 18. Second member 22 comprises a second trunk portion 24, a second midsection 26 comprising a second opening 27, and a second leg portion 28. First member 12 and second member 22 are adapted to interlock with one another in an assembled configuration in which second trunk portion 24 is coaxially contained within first trunk portion 14, second leg portion 28 protrudes through the first opening 17, and second opening 27 faces first leg portion 18. First opening 17 may have a greater area than the second opening 27. The shape of first opening 17 may generally be the shape of the outer periphery of the portion of second member 22 which extends through the opening. The shape of second opening 27 may generally be suitable to be an extension of the flow path defined by first member 12.

Figure 2:
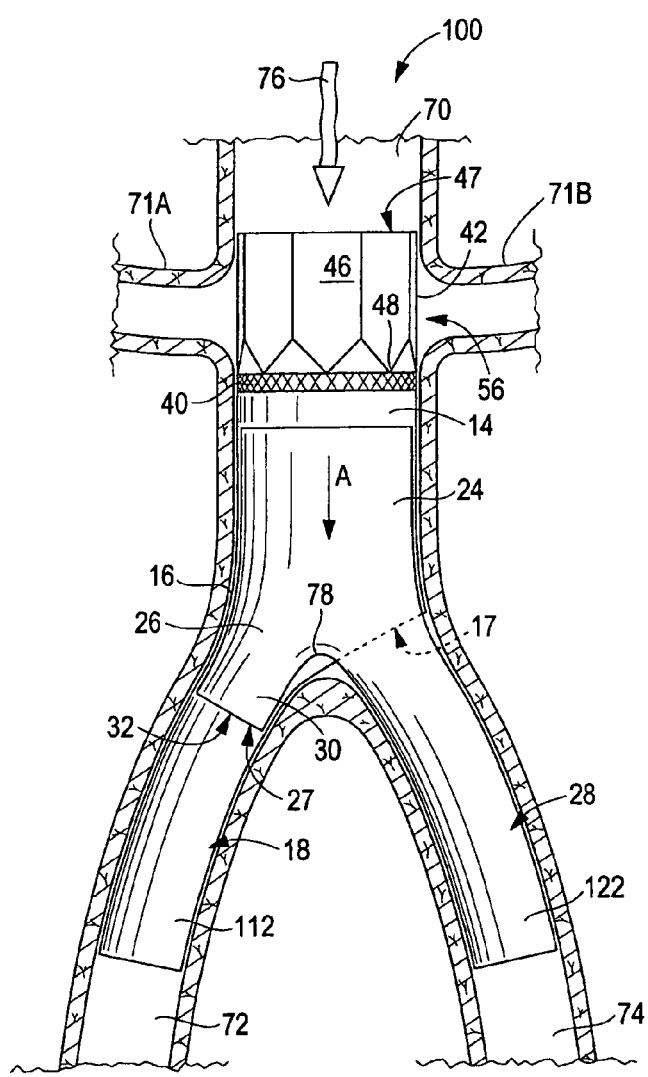
FIG. 2 is a longitudinal section view showing another exemplary embodiment of a device of the present invention.

Referring now to FIG. 2, there is shown another exemplary endoluminal device 100. Endoluminal device 100 also comprises first and second members 112 and 122, each having respective trunk portions 14 and 24, midsections 16 and 26, openings 17 and 27, and leg portions 18 and 28, similar to members 12 and 22. Second midsection 26 of second modular member 122, however, further comprises a leg stump portion 30 opposite leg portion 28. Leg stump portion 30 has an open end 32 comprising opening 27. Leg stump portion 30 is adapted to protrude into the first leg portion 18 when first member 112 and second member 122 are interlocked. Leg stump portion 30 serves to further stabilize second member 122 within first member 112, and may extend into leg portion 18 any suitable length.

Device 100 shown in FIG. 2 further comprises a seal ring 40 in trunk portion 14 of first member 112. Seal ring 40 may comprise any circumferential area of the device having greater sealing properties than the surrounding areas of the device. For example, device 100 may comprise a stent that exerts a certain radial force per unit length throughout the stent, but the seal ring portion exerts a greater radial force. Alternatively, the stent may have a covering comprising one type of material over much of the stent surface area and a different material in the area of the seal ring. For example, the material in the seal ring may comprise a knit material with a heavier texture than the surrounding material. The greater sealing properties of the underlying stent may result from the use of a first stent pattern, such as a woven mesh with a first amount of open area between filaments, in the area surrounding the seal ring, and a second stent pattern, such as a more densely woven mesh with a second, lesser amount of open area between filaments, in the seal ring itself. Other embodiments of seal rings suitable for use in this invention are disclosed in U.S. patent application Ser. No. 09/898,936 entitled IMPLANT HAVING IMPROVED FIXATION TO A BODY LUMEN AND METHOD FOR IMPLANTING THE SAME by Paul DiCarlo and filed on Jul. 3, 2001, incorporated herein by reference. Any seal ring embodiment may be used, however, such as but not limited to embodiments described in U.S. Pat. No. 5,575,818 to Pinchuk, incorporated herein by reference. Seal rings may be located anywhere along the body of the first or second member where desired. For example, seal rings may be particularly useful at the distal or proximal ends of the members for sealing against the lumen wall, as illustrated by seal ring 40. Seal rings may also be useful in the first member opening 17 or on the corresponding portion of second member 22 or 122 that is contacted by opening 17, to facilitate a stronger seal at the interface between the first and second members.

The respective members of endoluminal devices 10 and 100 may comprise a stent 42 having at least a partial covering 44 inside, outside, or inside and outside of the stent. The stent itself may be any type of stent known in the art, such as a filamentary stent or a stent fabricated by laser or otherwise cutting a preformed tube or sheet to be rolled into a tube. The stent may also comprise any stent material known in the art, such as a plastically deformable material such as stainless steel, or a superelastic material or shape-memory material, such as nitinol, or some combination thereof. Accordingly, the stent may be balloon expandable, self-expanding, or some combination thereof. The stent construction is not limited, however, to any particular design, architecture, fabrication method, deployment method, or materials.

Covering 44 may comprise a textile, such as a knit or woven textile, a plastic, such as ePTFE or urethane, or a combination thereof. Referring now to FIG. 3, there is shown a cross-section of an exemplary device taken across line 3—3 in FIG. 1, with the inner surface of the device at the bottom and the outer surface of the device at the top. As shown in FIG. 3, the device may comprise a stent 42 have both an outside ePTFE covering 50 and an inside ePTFE covering 52. The outside ePTFE covering 50 may further comprise a textile covering 54, such as a knit or woven covering as shown in FIG. 3. The textile covering may, for example, comprise stretchable PET or polyester yarn. In an alternative embodiment, the stent may have no inner ePTFE covering 52 or no outer textile covering 54. Any combination of the coverings, however, may be present.

The covering configuration may be the same throughout each member, or may vary in different areas according to need. For example, first member 112 may comprise an inside covering 52 and second member 122 may comprise an outside covering 50. The interlocking portion 60 of first member 12 that is adapted to contact the outside covering of the second member, however, may have no inside covering.

As shown in FIG. 2, first member 112 of device 100 may further comprise an uncovered portion 56 of stent 42. Uncovered portion 56 of stent 42 may comprise a hexagonal cell design, wherein each cell 46 typically has a pointed apex section 48 at opposite ends, or any design known in the art. As shown in FIG. 2, cells 46 are end cells that have pointed apex sections 48 at the proximal end and flat distal ends 47, providing pentagons rather than hexagons. The covered portion of stent 42 may comprise the same geometric pattern or a different pattern as the end geometry. For endoluminal device 100, which is shown mounted in a branched lumen, such as the aorta, uncovered portion 56 may be located at an intersection of branch lumens 71A and 71B, such as the intersection of the renal arteries with the aorta. Such a configuration prevents the stent covering from blocking blood flow to the branch arteries. Thus, as shown in FIG. 2, second trunk portion 24 of second member 122 is not distally coextensive with first trunk portion 14 of first member 112. That is, first trunk portion 14 comprises the uncovered portion 56 which extends further distally than trunk portion 24. In other designs, however, the two trunk portions may end at the same distal location.

As shown in FIG. 1, each member 12 and 22 has a tapered diameter throughout its entire length, tapering from a larger diameter at the distal end to a smaller diameter at the proximal end. In other designs, however, at least the leg portions may have a constant diameter, as shown in FIG. 2. The overall member design may differ for a tapering leg design as compared to a straight leg design. For example, referring now to FIGS. 4 and 5, there are shown a first member 212 with a tapered leg design and a first member 312 with a straight leg design, respectively. Opening 217 in tapered-leg first member 212 has essentially an tear-drop or egg shape, and the body of first member 212 has a smooth curvature. Opening 317 in straight-leg first member 312 has an almost triangular projection, whereas the body of first member 312 comprises three distinct sections, a larger diameter trunk portion 314, a tapered midsection 316, and a smaller diameter leg portion 318.

One advantage of the present invention is that the modular components may be similar in size and profile. For example, any endoluminal device typically has a compressed configuration and an expanded configuration, and each device has a respective diameter or profile in each configuration. For many bifurcated modular devices known in the art, the individual modular members may differ in compressed profile significantly enough that differently sized delivery systems may be required to deploy each member. As used herein, the term "profile" refers to the largest diameter of any portion of a device in a compressed configuration. For the design shown in FIG. 1, however, each of the modular members has a similar, if not identical, compressed profile, and can thus be introduced into the body using similarly sized delivery systems. Furthermore, because each member 12 and 22 comprises only a trunk section and a single leg, the delivery system may be relatively smaller than a delivery system designed to deploy a bifurcated device having a trunk section and at least a portion of two legs. Members 12 and 22 do not have a profile any larger than any non-branching device having a diameter the size of the diameter of trunk portion 14, and thus do not require a delivery system any larger than for such a non-branching device.

The similarity in profile and geometry of first member 12 and second member 22 also means that they can be constructed using similar tooling, and the simplicity of both means that they can be constructed without the need for any of the special or complex tooling typically required for bifurcated systems. The simplicity of design also makes the members relatively easier to cover using existing lamination and bonding techniques, resulting in reduced cycle time and higher yields as compared to traditional bifurcated devices.

The interlocking design of the device of this invention also provides certain advantages. As shown in FIG. 2, the device is typically deployed in a body lumen comprising a main lumen 70, a first branch lumen 72, a second branch lumen 74, and an internal fluid 76 flowing in a first direction along arrow A from the main lumen into the first and second branch lumens. First member 112 directs fluid 76 from main lumen 70 into first branch lumen 72 and second member 22 directs the fluid from the main lumen into second branch lumen 74. The shear force of fluid 76 flowing in the direction of arrow A tends to force second member 22 against first member 12 in a sealing relationship. That is, the fluid pressure wedges second member 22 further into opening 17 of member 12, strengthening the seal between opening 17 and the member 22. In particular, fluid 76 impinges against inner crotch 78 in second member 122 and adds to the force that interlocks members 112 and 122 together. In a design without a leg stump 30, such as the design shown in FIG. 1, there is a sharper transition between the midsection and the legs that may provide more advantageous hemodynamics because there is no dead space where clots can form.

The endoluminal device of the present invention may be introduced by any known surgical procedure. Preferably, the device is introduced endoluminally, by first introducing first member 12 to its location, in a proper radial orientation using radiopaque markers such that first opening faces second branch lumen 74 (as shown in FIG. 2). Then, second member 22 is deployed by directing a second introducer through first opening 17. In the embodiment shown in FIG. 1, second member 22 can be deployed directly to its ultimate location to be desired. In the embodiment shown in FIG. 2, however, it is desirable to initially deploy second member 122 at a location slightly upstream of its ultimate resting place to ensure that leg stump 30 leads to first branch lumen 32. Endoluminal fluid flow in the direction of arrow A may then move second member 122 proximally until crotch 78 of second member 122 abuts first member 112.

The deployed device may be inspected using fluoroscopy, optionally following injection of a contrast media, as is known in the art, to ascertain that the second member 122 has seated properly in abutment with first member 112. If necessary, mechanical means, such as but not limited to a hook or tethers attached to the second member, may be used to adjust the position of second member 122. As noted above, the stent may be deployed by any type of expansion known in the art. Regardless of how the stent is initially deployed, balloon devices may be used to model the members into place to conform to the topography of the lumen, as is known in the art.

First member 112 may be introduced from a proximal location downstream of the deployment location through first branch lumen 72, and second member 122 introduced from a proximal location through branch lumen 74, or one or both members may be introduced through main lumen 70 from proximal locations upstream of the deployment location.

Furthermore, although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. An endoluminal device comprising:
   a first member comprising a first trunk portion, a first midsection comprising a first opening, and a first leg portion comprising a first aperture;
   a second member comprising a second trunk portion, a second midsection comprising a second opening, and a second leg portion comprising a second aperture
   wherein each of the first member and the second member comprises a stent having a covering inside, outside, or inside and outside of the stent, the device having an assembled configuration in which the first member and second member are interlocked with one another in a sealing relationship in which the second trunk portion is coaxially contained within, and sealed against, the first trunk portion, the second leg portion protruding through the first opening, and the second opening facing the first leg portion.

2. The endoluminal device of claim 1, wherein the second midsection further comprises a leg stump portion that protrudes into the first leg portion of the first member in the assembled configuration.

3. The endoluminal device of claim 1, wherein the first member further comprises a seal ring.

4. The endoluminal device of claim 1, wherein the covering comprises a textile, a plastic, or a combination thereof.

5. The endoluminal device of claim 1, wherein the covering comprises a knit or woven textile.

6. The endoluminal device of claim 1, wherein the covering comprises ePTFE or urethane.

7. The endoluminal device of claim 4, wherein each of the stents of the first member and the second member comprises an outside ePTFE covering.

8. The endoluminal device of claim 7, wherein each of the stents further comprises an inside ePTFE covering.

9. The endoluminal device of claim 7, wherein each of the stents further comprises an additional covering over the outside ePTFE covering.

10. The endoluminal device of claim 9, wherein the additional covering comprises a textile covering.

11. The endoluminal device of claim 10, wherein the textile covering comprises a knit covering.

12. The endoluminal device of claim 10, wherein the textile covering is stretchable.

13. The endoluminal device of claim 10, wherein the textile covering comprises PET or polyester yarn.

14. The endoluminal device of claim 8, wherein each of the stents further comprises a knit PET or polyester yarn covering over the outside ePTFE covering.

15. The endoluminal device of claim 1, wherein the first member further comprises an uncovered portion of the stent.

16. The endoluminal device of claim 15, wherein the device is adapted to be mounted in an aorta and the uncovered portion is adapted to be located at an intersection of a renal lumen with the aorta.

17. The endoluminal device of claim 1, wherein each of the first member and the second member has a tapered diameter.

18. The endoluminal device of claim 1, wherein each of the first leg portion and the second leg portion has a constant diameter.

19. The endoluminal device of claim 1, wherein the second trunk portion is not distally coextensive with the first trunk portion.

20. The endoluminal device of claim 19, wherein the first member comprises an uncovered portion located distally of a distal end of the second member.

21. The endoluminal device of claim 1, wherein the first member comprises a partial inside covering and the second member comprises an outside covering, wherein the first member comprises an interlocking portion adapted to contact the outside covering of the second member, the interlocking portion having no inside covering.

22. The endoluminal device of claim 1, wherein the first opening comprises a greater open area than the second opening.

23. The endoluminal device of claim 1, wherein each of the first member and the second member has an essentially equivalent compressed profile.

24. A modular endoluminal device for deployment in a body lumen comprising a main lumen, a first branch lumen, a second branch lumen, and an internal fluid flowing in a first direction from the main lumen into and through the first branch lumen and the second branch lumen, the device comprising a first member for directing the fluid from the main lumen into the first branch lumen and a second member for directing the fluid from the main lumen into the second branch lumen, wherein each of the first member and the second member comprises a stent having a covering inside, outside, or inside and outside of the stent, the first member and the second member adapted to interlock together such that the fluid flow forces the second member against the first member in a sealing relationship.

25. The device of claim 24, wherein the second member comprises at least one impingement area on which the fluid flow impinges to force the second member against the first member.

26. The endoluminal device of claim 24, wherein the first member comprises a first trunk portion, a first midsection comprising a first opening, and a first leg portion; the second modular member comprises a second trunk portion, a second midsection comprising a second opening, and a second leg portion; and the first member and second member interlock with one another in an assembled configuration in which the second trunk portion is coaxially contained within, and sealed against, the first trunk portion, the second leg portion protrudes through the first opening, and the second opening faces the first leg portion.

27. The endoluminal device of claim 25 wherein the second midsection further comprises a leg stump portion that protrudes into the first leg portion of the first member in the assembled configuration.

28. A system for deployment of an endoluminal device, the system comprising:
   the endoluminal device comprising a first member having a first trunk portion, a first midsection comprising a first opening, and a first leg portion comprising a first aperture; and a second member having a second trunk portion, a second midsection comprising a second opening, and a second leg portion comprising a second aperture;
   a first introducer for deploying the first member into a body lumen and having a first profile; and
   a second introducer, having a second profile essentially identical to the first profile, for deploying the second member into the body lumen;
   wherein each of the first member and the second member comprises a stent having a covering inside, outside, or inside and outside of the stent, the device having an assembled configuration in which the first member and second member are interlocked with one another in a sealing relationship with the second trunk portion coaxially contained within, and sealed against, the first trunk portion, the second leg portion protruding through the first opening, and the second opening facing the first leg portion.

29. A method of deploying an endoluminal device in a deployment location in a branched lumen comprising a main lumen, a first branch lumen, and a second branch lumen, the endoluminal device comprising a first member comprising a first trunk portion, a first midsection comprising a first opening, and a first leg portion comprising a first aperture; and a second member comprising a second trunk portion, a second midsection comprising a second opening, and a second leg portion comprising a second aperture, each of the first member and the second member comprises a stent having a covering inside, outside, or inside and outside of the stent; the method comprising the steps of:
  (a) inserting a first introducer containing the first member into the branched lumen from a first proximal location;
  (b) deploying the first member with the first trunk portion in the main lumen and the first leg portion in the first branch lumen;
  (c) inserting a second introducer containing the second member into the branched lumen from a second proximal location;
  (d) deploying the second member such that the second member is interlocked with the first member in a sealing relationship with the second trunk portion coaxially contained within, and sealed against, the first trunk portion, the second leg portion protruding through the first opening into the second branch lumen, and the second opening facing the first leg portion.

30. The method of claim 29 wherein at least one of the first proximal location and the second proximal location is located downstream of the main lumen.

31. The method of claim 29 wherein at least one of the first proximal location and the second proximal location is located upstream of the main lumen.

32. The method of claim 29 wherein the endoluminal device further comprises a stent having a covering inside, outside, or inside and outside of the stent, and an uncovered portion of the stent, and the branched lumen further comprises at least a third branch upstream of the first branch and second branch, the method further comprising aligning the device such that the uncovered portion is located at an intersection of the third branch with the main lumen.

33. The method of claim 29 wherein the method comprises deploying the device in an aorta, wherein the first branch and the second branch each comprise iliac arteries.

34. The method of claim 32 wherein the method comprises deploying the device in an aorta, wherein the first branch and the second branch each comprise iliac arteries and the third branch comprises a renal artery.

35. The method of claim 29 wherein the second midsection further comprises a leg stump portion that protrudes into the first leg portion of the first member in the assembled configuration and a crotch connecting the leg stump portion to the second leg portion, the assembled configuration comprising a configuration wherein the second member crotch abuts the first member in a final resting position, the method further comprising deploying the second member slightly upstream of the final resting position and allowing endoluminal fluid flow to move the second, member downstream into the final resting position.

36. The method of claim 29 wherein the first member comprises a partial inside covering and the second member comprises an outside covering, the first member comprising an interlocking portion having no inside covering, wherein the method further comprises deploying the second member such that the outside covering of the second member is in contact with the interlocking portion of the first member.

* * * * *